(12) United States Patent
Kemeny

(10) Patent No.: US 8,967,851 B1
(45) Date of Patent: Mar. 3, 2015

(54) SPECTRAL MONITORING OF INGREDIENT BLENDING

(75) Inventor: Gabor J. Kemeny, Middleton, WI (US)

(73) Assignee: Kemeny Associates, Middleton, WI (US)

(*) Notice: Subject to any disclaimer, the term of this patent is extended or adjusted under 35 U.S.C. 154(b) by 317 days.

(21) Appl. No.: 13/353,872

(22) Filed: Jan. 19, 2012

Related U.S. Application Data (60) Provisional application No. 61/434,154, filed on Jan. 19, 2011.

(51) Int. Cl.
 *B01F 15/00* (2006.01)
 *B01F 15/06* (2006.01)

(52) U.S. Cl.
 USPC ............................................. 366/143; 366/142

(58) Field of Classification Search
 CPC ... B01F 7/00933; A01C 1/00; B01J 2219/182
 USPC .................................................. 366/143, 250
 See application file for complete search history.

(56) References Cited

U.S. PATENT DOCUMENTS

| | | | |
|---|---|---|---|
| 4,283,148 A * | 8/1981 | Peterson | 366/142 |
| 4,769,830 A * | 9/1988 | Peterson et al. | 378/54 |
| 6,070,128 A | 5/2000 | Descales et al. | |
| 6,483,112 B1 | 11/2002 | Lewis | |
| 6,629,041 B1 | 9/2003 | Marbach | |
| 6,690,464 B1 | 2/2004 | Lewis et al. | |
| 7,075,645 B2 * | 7/2006 | Gehrlein et al. | 356/328 |
| 7,255,474 B2 | 8/2007 | Cong et al. | |
| 7,277,168 B2 | 10/2007 | Walker | |
| 7,391,025 B2 | 6/2008 | Lewis | |
| 7,399,968 B2 | 7/2008 | Lewis et al. | |
| 7,456,952 B2 | 11/2008 | Walker | |
| 7,567,871 B2 | 7/2009 | Rohde et al. | |
| 7,812,939 B2 | 10/2010 | Merrill, II et al. | |
| 7,864,316 B2 | 1/2011 | Lewis et al. | |
| 7,924,414 B2 | 4/2011 | Mound | |
| 2003/0095470 A1 * | 5/2003 | Afnan et al. | 366/142 |
| 2007/0247965 A1 * | 10/2007 | Sanders et al. | 366/143 |

OTHER PUBLICATIONS

Spectral Dimensions Inc., Chemical Imaging Solution visualizes ingredient blending, 2005.

Spectral Dimensions Inc., Spectral Dimensions Announces Successful Deployment of a Chemical Imaging Solution for Visualizing Pharmaceutical Ingredient Blending, 2005.

* cited by examiner

*Primary Examiner* — Tony G Soohoo
*Assistant Examiner* — Anshu Bhatia
(74) *Attorney, Agent, or Firm* — Craig A. Fiescho, Esq.; DeWitt Ross & Stevens S.C.

(57) ABSTRACT

Spectral and hyperspectral imaging systems allow monitoring of pharmaceutical or other industrial blending processes to establish the characteristics of the blend. To illustrate, a batch type blender may be equipped with a computer controlled drive mechanism that is slowed down at a predetermined point during rotation to assess the progress of the blending through an imaging window mounted on the blender. A fast hyperspectral imaging device can be provided directly on the blender to view the blend through the imaging window, or can be placed in a fixed position relative to the rotating blender. The image of the blend is preferably captured line-by-line at a location at or near the bottom of the blender synchronously with the blender's rotation. The spectral information acquired from the blend at each rotation can be used to assess whether the nominal blend composition is achieved, or to reveal uniformity of the blend.

18 Claims, 6 Drawing Sheets

SPECTRAL MONITORING OF INGREDIENT BLENDING

CROSS-REFERENCE TO RELATED APPLICATIONS

This application claims priority under 35 USC §119(e) to U.S. Provisional Patent application 61/434,154 filed 19 Jan. 2011, the entirety of which is incorporated by reference herein.

FIELD OF THE INVENTION

This document concerns an invention relating generally to analysis of blends (particularly pharmaceutical mixtures) during the blending process, and more specifically to spectral and/or hyperspectral analysis during blending.

BACKGROUND OF THE INVENTION

In many fields of industry, e.g., chemical/pharmaceutical manufacturing, food processing, metallurgy/materials engineering, etc., it is often necessary to blend different ingredients to attain some desired mixture. It can be useful to monitor the properties of the mixture during blending to verify that the blending process is proceeding as planned. In some cases, it may be desirable to monitor changes in composition, phase, or other properties of the ingredients in the mixture, as can often occur where the mixture is reactive, or where it is heated or otherwise acted upon during blending. In other cases, it may simply be desirable to monitor the properties of the mixture during blending to confirm the degree of blending, i.e., whether the blend ingredients are mixed to the desired degree. Looking specifically to the field of pharmaceutical manufacturing as an example, active pharmaceutical ingredients (API) and excipients such as disintegrans, flow agents, binders, fillers and other ingredients are often blended before being tableted or filled into capsules. Each unit of the formulation, e.g., any single tablet or capsule, should contain a predetermined amount of API, and should dissolve at a predetermined rate, and reproducibly uniform and complete blending is needed to achieve this objective.

To control time and costs, it is desirable to cease blending as soon as mixing appears to be sufficiently thorough. Blending is a complex process because sometimes intensifiers need to be used to break up aggregates and sometimes it is necessary to limit the amount of mechanical energy imparted to the mixture. Ingredients are usually mixed in batches by tumbling or otherwise agitating them in a mixing bin, with the mixing bin having sufficient free space, and a suitable tumbling or agitation speed that the ingredients uniformly commingle over time as blending proceeds. Batch-type blenders using closed mixing bins having a variety of shapes are known, typically square bins, drum-like shapes or V-shapes, with ingredients typically being blended therein for a predetermined amount of time, or until a predetermined number of revolutions or oscillations are done. To facilitate emptying, the mixing bins typically have controls which cease bin motion when the bin is oriented such that an emptying port is situated at or near the bottom of the bin. The content of the bin can be examined by pulling samples from different depths through ports in the bin while the bin is stationary. Manufacturers often verify blending by sampling and testing a blend after a predetermined amount of blending has occurred, e.g., after a predetermined blending time, or after a predetermined number of rotations of a batch-type blender rotating at a predetermined rate. The blender is stopped and a sample is taken to a laboratory and examined using conventional analytical methods such as molecular spectroscopy, wherein the sample is illuminated, often with non-visible light such as light in the infrared region of the spectrum, and the light reflected by, transmitted through, and/or not absorbed by the specimen is then captured and analyzed to reveal information about the characteristics of the specimen. As an example, a specimen may be illuminated with near-infrared light having known intensity across a range of wavelengths, and the light from the specimen can then be captured for comparison to the illuminating light. Review of the captured spectra (i.e., light intensity vs. wavelength data) can then illustrate the wavelengths at which the illuminating light was absorbed by the specimen, which in turn can yield information about the chemical bonds present in the specimen, and thus its composition and other characteristics. Libraries of spectra obtained from reference specimens of known composition are available, and by matching measured spectra versus these reference spectra, one can then determine the composition of the specimens from which the measured spectra were obtained.

Periodic halting of the batch-type blender to collect and test samples is disadvantageous because it interrupts the blending process and increases the time needed for blending. It might be assumed that manufacturers could instead simply start blending ingredients, and later cease blending at some time in the future when complete blending might be presumed. However, this is not always the case. "Overblending" (i.e., blending for longer than needed) can sometimes lead to adverse effects since some mixture ingredients may initially disperse, but then undesirably re-aggregate over time.

Continuous blending systems are also used. These typically have an inlet, an outlet, and some means to mix the ingredients as they are transferred from the unblended state at the inlet to the blended state at the outlet. Samples can be collected, or the blend can otherwise be observed, at locations along the blender or at its outlet. Continuous blending systems are often unsuitable owing to the size/length of the blender needed to obtain the desired degree of mixing, the difficulty typically encountered with reconfiguring the blender to accommodate different blends, and/or owing to the aforementioned need to optimize mechanical energy input to the blend ingredients.

Attempts have been made to reduce the time and burden of blend testing in batch-type blenders. At-line methods, wherein the blender is stopped and a sample is analyzed in an instrument situated in close proximity to the blender, have been used to assess the degree of blending. Additionally, instruments have been modified for use directly on the blenders themselves. To illustrate, spectrometers (typically near-infrared and fluorescence spectrometers) have been built as portable modules and are detachably affixed to blenders' mixing bins. The blend ingredients are placed in a blender, and during blending, the ingredients tumble over an observation window in the mixing bin, covering the window when it is at or near the bottom of the rotating bin and uncovering it when it is at or near the top of the rotating bin. The spectrometer directs input light through the window and captures the spectra of output light scattered/reflected from the blend as it covers the window, with this light being characteristic of the blend's properties (more particularly, of the blend's average or bulk properties, as represented by the mixture resting across the area of the window from which the output light is captured). The spectrum changes as blending progresses, and the blend is assumed to be finished when the spectrum does not change any further. These types of "on-bin" devices have limited performance capabilities because of space and weight limitations for the blenders' mixing bins. Additionally, such "on-bin" devices typically require time-consuming pre-blending calibration, wherein known mixtures are analyzed prior to blending to establish datum points (e.g., reference spectra) for subsequent measurements.

A review of this type of analysis reveals that capturing one bulk spectrum per rotation of the blender provides insufficient analytical information about the degree of mixedness and the relative positions of the blend ingredients, and fails to recognize the conditions under which blend ingredients begin re-aggregating. There is significant interest in additional and improved arrangements for obtaining information regarding the distribution and uniformity of blend ingredients in a rapid and accurate manner which offers little or no interference to the blending process.

SUMMARY OF THE INVENTION

The invention, which is defined by the claims set forth at the end of this document, is directed to arrangements for monitoring blends which at least partially address the foregoing issues. A basic understanding of some of the features of preferred versions of the invention can be attained from a review of the following brief summary of the invention, with more details being provided elsewhere in this document. To assist in the reader's understanding, the following review makes reference to the accompanying drawings (which are briefly reviewed in the "Brief Description of the Drawings" section following this Summary section of this document).

Figure 1A:
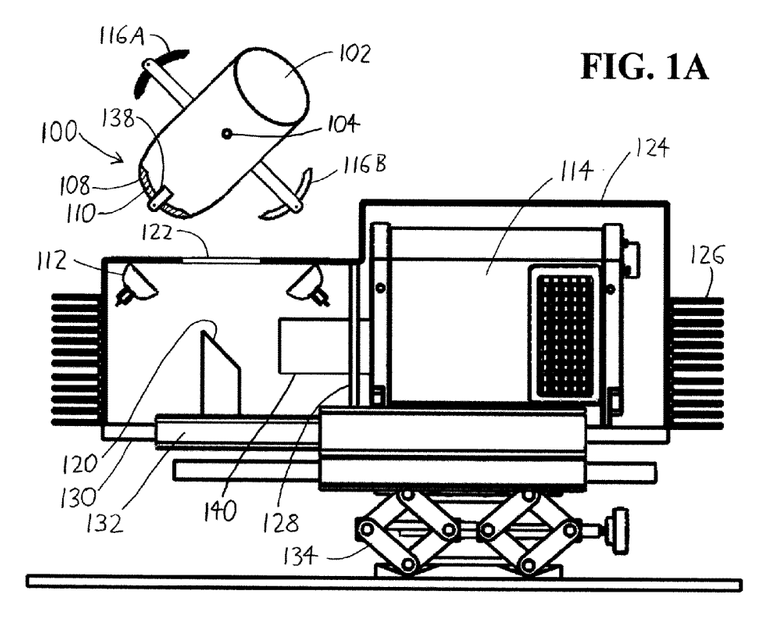
FIG. 1A is a schematic side elevational view of an exemplary blending system, showing a rotating mixing chamber 102 having an imaging window 110 through which a camera 114 may spectrally image the blend ingredients being mixed within the mixing chamber 102.
Figure 1B:
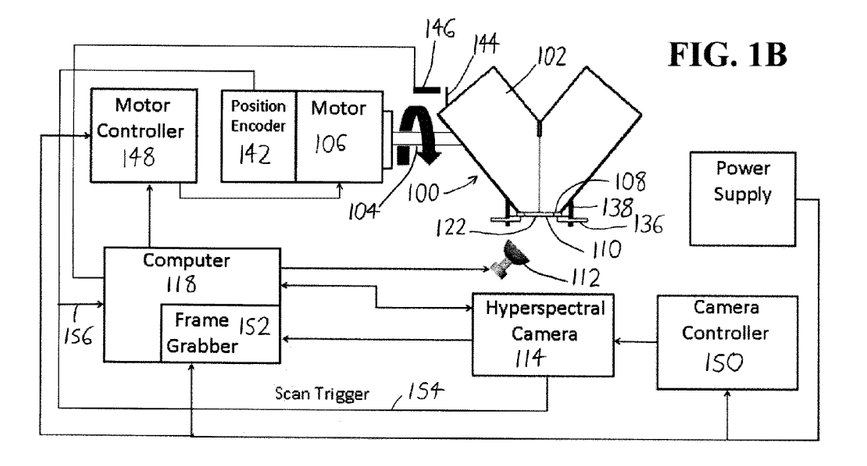
FIG. 1B is a schematic depiction of possible components of the blending system of FIG. 1A and the communications therebetween, as well as a schematic cross-sectional view of the mixing chamber 102 depicted in FIG. 1A (as seen from its front).

Referring to FIGS. 1A and 1B, an exemplary version of the blending system includes a blender 100 (e.g., for ingredients for a pharmaceutical product), with the blender 100 here having a mixing chamber 102 configured to receive ingredients to be mixed, and an actuator (not shown in FIG. 1A) configured to move the mixing chamber 102 to agitate and mix any ingredients therein. The mixing chamber 102 of the blender 100 is depicted in FIG. 1B as a V-shaped mixing bin which is rotated about a tumbling axis 104 by an actuator 106 in the form of a rotary motor. The mixing chamber 102 is fully enclosed, and its interior enclosure can be accessed to supply ingredients to be mixed, or to remove mixed ingredients, via one or more ports 108 openable onto and closable upon the mixing chamber 102. An imaging window 110 is situated on the mixing chamber 102 (here on the port 108), and is formed of solid material which is at least substantially transparent to one or more wavelengths of light (those wavelengths over which spectra of the blend ingredients are desired).

A light source 112 is situated adjacent the mixing chamber 102, and is aligned with the imaging window 110 to illuminate any ingredients within the mixing chamber 102. This illumination occurs on a periodic basis in FIGS. 1A-1B as the imaging window 110 rotates into the path of the beam of the light source 112.

A camera 114 is also situated adjacent the mixing chamber 102, and is aligned with the imaging window 110 to capture a set of spectra from any illuminated ingredients within the mixing chamber 102 next to the imaging window 110. This spectral capture also occurs on a periodic basis in FIGS. 1A-1B, with the camera 114 being mounted in a fixed position adjacent a path traveled by the imaging window 110 such that it is stationary during rotation of the mixing chamber 102, and capturing the spectra as the imaging window 110 rotates into alignment with the camera 114. The camera 114 preferably captures successive sets of spectra in a "pushbroom" fashion as the imaging window 110 travels past the camera 114, with each set containing spectra from a row of contiguous areas next to the imaging window 110 (with the row being parallel to the axis of rotation of the mixing chamber 102).

Most preferably, the camera 114 captures spectra along successive rows of pixels which are collected as the mixing chamber 102 rotates, such that the successive rows of pixels collectively form an image of the ingredients within the mixing chamber 102 next to the imaging window 110. The ingredients within the mixing chamber 102 are therefore "hyperspectrally" imaged, wherein a spectrum is captured for each pixel of the image, thereby providing data on the imaged ingredients in two spatial dimensions and one spectral dimension (wherein the spectral dimension is typically a range of wavelengths of interest, though it could alternatively or additionally include discrete wavelengths of interest).

The imaging window 110 of the mixing chamber 102 is preferably curved, at least at its inner window surface, such that the camera 114 can consistently focus on and image the mixing ingredients on and/or adjacent to the concavely curved inner window surface during rotation of the mixing chamber 102. An imaging window 110 having a different contour (e.g., planar) may be used instead, but such an arrangement can lead to distortion since spectra may be captured from rows of areas at different distances from the camera 114. Depending on the camera 114 speed and the speed of data transmission therefrom, the actuator 106 might be controlled such that it moves the mixing chamber 102 at a slower speed when the camera 114 is aligned with the imaging window 110, e.g., it may slow its rotational speed as the imaging window 110 passes the camera 114 so that more time is available to capture each set of spectra. Such an arrangement is also useful where the camera 114 implements other imaging arrangements, e.g., a "staring array" arrangement where the camera 114 simultaneously images the entire field to be imaged within the mixing chamber 102 next to the imaging window 110, but does so one wavelength at a time. As examples, the light source 112 could be sequentially tuned to desired wavelengths of light to be transmitted to the field, and/or the light received by the camera 114 can be filtered to pass the light scattered/reflected from the field to the camera 114 one wavelength (or a few wavelengths) at a time. Despite the foregoing, arrangements which do not require slowing or stopping of the motion of the mixing chamber 102 are preferred, since these tend to more quickly yield a finished blend, and better simulate the continuous blending typically used during industrial blend production.

For easier calibration of measurements, the mixing chamber 102 may also include one or more reference windows 116A/116B on the mixing chamber 102 spaced from the imaging window 110, wherein the reference windows 116A/116B also periodically align with the camera 114 as the mixing chamber 102 moves. These reference windows 116A/116B can be formed of materials which generate reference spectra, e.g., pure ingredient spectra, high level diffuse reflectance spectra representative of the incident illumination from the light source 112, spectra representative of the background noise of the camera 114, etc. As examples, FIG. 1A illustrates a white or totally reflective reference window 116A which can be imaged to capture reference spectra representative of the incident illumination, as well as a black or totally absorbent reference window 116B which can be imaged to capture reference spectra representative of the camera 114's background noise level. As with the imaging window 110, any reference windows 116A/116B on the mixing chamber 102 are preferably curved so that an at least substantially constant distance is maintained between the reference window(s) and the camera 114 during rotation of the mixing chamber 102.

The spectra captured by the camera 114 can be provided to a processor (e.g., a computer 118, FIG. 1B) to generate a measure of the uniformity of the distribution of the ingredients within the mixing chamber 102 (i.e., the uniformity of the mixture), preferably after adjusting the spectra to account for any reference spectra. As an example, the processor 118 could generate a display illustrating changes in spectral intensity at each pixel over time at two or more wavelengths, in particular, at wavelengths corresponding to the ingredients in the mixture, thereby illustrating changes in concentration of the ingredients over the imaged field over time. To illustrate, FIG. 2A contains sets (columns) of images wherein each set contains images representing the concentration of blend ingredients calculated from spectra obtained at the same time (e.g., after the mixing chamber 102 has undergone some number X of rotations), and different sets (different columns) contain images representing spectra obtained at different times. Further, each image within each set represents the imaged field within the mixing chamber 102 next to the imaging window 110, with each image displaying the concentration of one of the ingredients in the mixture, as derived from the spectral intensity or intensities at that ingredient's "signature" wavelength(s). The FIG. 2A display therefore illustrates the concentration of each ingredient across the field over time.

Figure 3A:
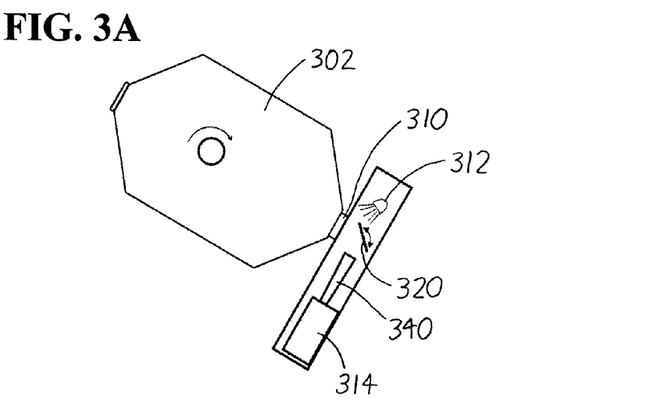
FIG. 3A is a schematic representation of an alternative blending system wherein the imaging system (the camera 314, its light source 312, etc.) is mounted on, and rotates with, the mixing chamber 302.

The foregoing camera imaging schemes, and the processing and display of spectra, can also be implemented in other mixing chamber arrangements. As an example, FIG. 3A illustrates an arrangement wherein the light source 312 and camera 314 travel with the mixing chamber 302, with the camera 314 imaging the mixing ingredients through the imaging window 310 at a time when the imaging window 310 is situated at least partially vertically above the camera 314 (and thus the ingredients being mixed have fallen atop the imaging window 310). If this arrangement is used along with the aforementioned "staring array" imaging scheme wherein spectra are captured wavelength-by-wavelength over the entire field to be imaged, it is recommended that the rotation (or other motion) of the mixing chamber 302 be slowed or halted during imaging to such an extent that the ingredients being imaged atop the window do not shift during imaging. If necessary or useful, motion of the material chamber can also be slowed or halted where the material is imaged row by row in "pushbroom" fashion (as by pivoting the mirror 320), with a range of wavelengths being captured at each row.

Figure 4:
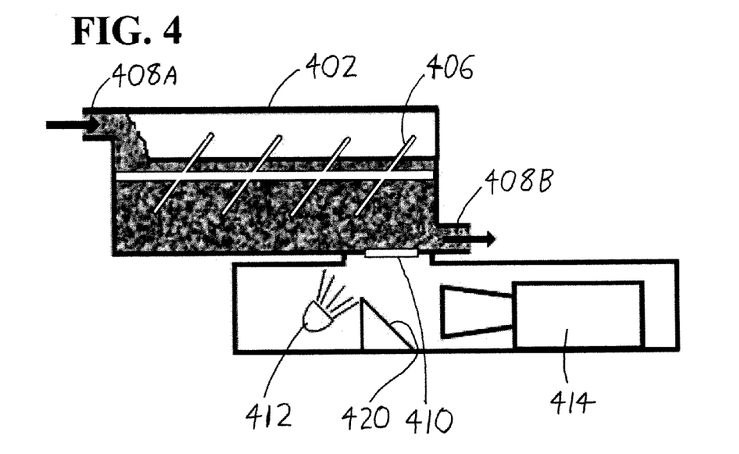
FIG. 4 is a schematic representation of a blending system wherein the imaging system (the camera 414, its light source 412, etc.) images blend ingredients as they are continuously mixed within, and urged through, the mixing chamber 402.

FIG. 4 illustrates another exemplary arrangement wherein the mixing chamber 402 has an inlet port 408A and an exit port 408B, and an actuator 406 (such as paddles or a screw drive) mixes materials as they are continuously transported through the mixing chamber 402 from the inlet port 408A to the exit port 408B. A light source 412 can illuminate the mixing ingredients through an imaging window 410, and a camera 414 can capture spectra row-by-row in such a manner that a continuous spectral image of the ingredients flowing against the imaging window 410 is captured. Alternatively, a field across the imaging window 410 can be imaged while rapidly scanning across multiple wavelengths, but here it may be necessary that the actuator 406 halt mixing (and thus halt motion of the ingredients against the imaging window 410) during imaging, so that the material across the field being imaged does not change as the camera 414 indexes through the wavelengths.

Further advantages, features, and objects of the invention will be apparent from the remainder of this document in conjunction with the associated drawings.

DETAILED DESCRIPTION OF PREFERRED VERSIONS OF THE INVENTION

Expanding on the discussion above, a first preferred version of the blending system is depicted in FIG. 1A, wherein a rotating mixing chamber 102 (a mixing bin) is configured to rotate about a tumbling axis 104. The mixing chamber 102 has a port 108 for filling and emptying ingredients to be mixed, wherein the port 108 has an imaging window 110 thereon. A camera 114 is situated adjacent the mixing chamber 102 such that the imaging window 110 rotates into the field of view of the camera 114, which is imaged via a directing mirror 120 through a viewing window 122 and onto the imaging window 110. One or more light sources 112, e.g., quartz halogen lights, are directed to evenly illuminate the field of view, and may include diffusers, lenses, or other optics to provide such even illumination of the field of view. A housing 124 bearing the viewing window 122 is shown in cross-section to reveal the camera 114, the directing mirror 120, the light sources 112, etc., which the housing 124 protects. The housing 124 preferably includes cooling fins 126, as well as fans and/or other cooling systems (not shown), to extract the heat generated by the light sources 112 and the camera 114. Insulation 128 is also preferably situated between the light sources 112 and the camera 114 to protect the camera 114 from the heat of the light sources 112.

The housing 124 and mixing chamber 102 are preferably designed as modules which are removable, or at least respaceable, from each other so that a container may be placed under the mixing chamber 102 to empty it, so that differently sized and/or differently configured mixing chambers 102 may be installed, so that easier camera 114 maintenance may be effected, etc. In FIG. 1A, this is done by situating the housing 124 on a base 130 attached to a lateral adjustment mechanism 132 (here shown as a set of slides, i.e., rails which are supported within tracks by bearings), whereby the housing 124 can be moved from under the mixing chamber's port 108. The slide mechanism 132 is in turn attached to a height adjustment mechanism 134, here depicted as a scissors lift, so that the camera 114 may adapt to different sizes and configurations of mixing chambers 102, so that the focus of the camera 114 can be more easily adjusted onto the ingredients just inside the imaging window 110 of the mixing chamber 102, etc.

The mixing chamber 102 of FIG. 1A is configured as a V-blender, and is schematically depicted from its front in a cross-sectional view in FIG. 1B (as opposed to the side view of FIG. 1A). Referring to FIG. 1B, the port 108 bearing the imaging window 110 is preferably configured as a removable metal plate held securely to the body of the mixing chamber 102 (preferably with an intervening gasket, not shown) by an off-axis key 136 extending from mounting arms 138 fixed to the body of the mixing chamber 102. Other attachment mechanisms, such as Tri-Clamp™ fittings may also be applied (Alfa Laval AB, Sweden). Returning to FIG. 1A, the imaging window 110 is preferably configured with a cylindrical inner surface (and preferably a cylindrical outer surface as well) having an at least substantially constant radial distance from the tumbling axis 104, such that the inner surface of the imaging window 110 (and thus the material being imaged) maintains a constant distance from the camera 114, thereby avoiding the need to synchronously adapt the focal distance of the camera 114 to the inner surface of the imaging window 110 as the mixing chamber 102 rotates (assuming imaging occurs during rotation of the mixing chamber 102, as discussed below). Other imaging window 110 shapes are possible, e.g., a planar imaging window 110 might be sufficient if the focal distance change is within the depth of focus of lens 140. The imaging window 110 can be formed of glass or other material (e.g., sapphire) appropriate for the wavelength range in which the spectral measurements are performed. In the near-infrared regions, e.g., in the near-infrared or NIR range (typically in the 1000-1700 nm range), or the short-wave infrared or SWIR range (typically in the 1000-2500 nm range), borosilicate, quartz, calcium fluoride ($CaF_2$), barium fluoride ($BaF_2$), and/or other glasses can be used. The imaging window 110 may be made of sapphire or coated with other materials which reduce adhesion of the ingredients being mixed. Preferably, the imaging window 110 is mounted such that it is flush with the inner contour of the port 108 to avoid unwanted stagnation and accumulation of mixing ingredients around the imaging window 110. Depending on the design of the mixing chamber 102, more than one imaging window 110 may be provided for imaging, e.g., a number of similarly-configured windows 110 may be situated about the circumference of a cylindrical mixing chamber 102.

FIG. 1A also illustrates arms on the mixing chamber 102 which bear reference windows 116A/116B which help establish datum measurements for captured spectra. While these are referred to as "windows," it should be understood that they will generally not be transparent to incident light. A reflective reference window 116A, which may be formed of optically white materials such as porous polytetrafluoro-ethylene (PTFE), can diffusely reflect the incident light from the light source(s) 112 to establish maximum measured intensities across the wavelengths of interest. Similarly, an absorbing reference window 116B, which may be formed of optically black materials such as compressed charcoal (perhaps with a small amount of binder), can absorb the incident light from the light source(s) 112 to establish minimum measured intensities (i.e., the background noise of the detector) across the wavelengths of interest. (Alternatively, such a spectral "background" can be measured from the camera 114 when a shutter arrangement prevents light from reaching the camera 114.) These reference windows 116A/116B are preferably configured to have the same radial distance from the tumbling axis 104 as the interior of the imaging window 110, such that they are also located at the focus of the camera 114. The reference windows 116A/116B need not both be provided, and/or could be provided on the port 108 (or on additional ports, if the mixing chamber 102 has additional ports), and could be installed at different times (e.g., they might be sequentially installed in place of the port 108 bearing the imaging window 110 to establish datum measurements prior to capturing spectra from a blend). Furthermore, they need not be situated on the mixing chamber 102, and could be provided on another item of equipment which moves into the view of the camera 114, or the view of the camera 114 could periodically be switched to stationary or moving reference windows situated off of the mixing chamber 102 (e.g., by use of a moving directing minor 120 or other optical component that redirects imaging to the reference windows). Other types of reference windows could be used as well, such as reference windows having the same spectral signature as ingredients of interest in a blend. In this respect, a reference window could be formed as a small sample chamber having its own imaging window 110, whereby blend ingredients can be installed in different sample chambers situated about the mixing chamber 102 so that the camera 114 may capture the spectra of pure ingredients. One or more of the foregoing reference windows 116A/116B, or a different reference window, could also be provided for the purpose of adjusting the focus of the camera 114, e.g., it may simply be a mask with a line pattern whereby the position of the camera 114 may be modified, and/or the focus of its lens 140 may be adapted, until the line pattern is in sharp focus.

The camera 114 in the foregoing arrangement is preferably a hyperspectral camera of the "pushbroom" type, wherein spectra across all wavelengths of interest are simultaneously captured at areas (pixels) along a row, and rows are sequentially captured across the imaging window 110 until an area of interest is fully spectrally imaged. More particularly, the camera 114 includes a spectrograph (e.g., a transmission or reflection grating) and a focal plane array detector (an array of photosensitive sensors), with these components not being depicted in the drawings. The camera lens 140 images the blend ingredients adjacent the imaging window 110 onto the spectrograph, which produces a spectrum from the image and projects it onto the focal plane array detector. The detector thereby receives a row of spectra corresponding to the imaged row along the blend ingredients, and the array of sensor elements (pixels) within the detector provide a corresponding array of spectral intensity measurements. The rows are captured synchronously with the rotation of the mixing chamber 102 via an arrangement such as that schematically illustrated in FIG. 1B, wherein an actuator 106 (e.g., a computer-controlled DC servomotor, a stepper motor, or another motor) rotates the mixing chamber 102 about its tumbling axis 104 (defined by a shaft), with an encoder 142 monitoring the rotational position of the mixing chamber 102. A position marker 144 and proximity sensor 146 (e.g., an optical or magnetic switch), not shown in FIG. 1A, are also preferably provided to detect a datum position of the mixing chamber 102 (e.g., a full vertical orientation), thereby providing an indication of an absolute position at which measurements begin, and from which the encoder 142 can accurately track the relative position of the mixing chamber 102. The light source(s) 112 illuminate the focal line imaged by the camera 114 as the mixing chamber 102 rotates, with the control computer 118 controlling the motor 106 via a motor controller 148. At the same time, the output of the encoder 142 is supplied to a camera controller 150 which synchronously controls the camera 114 to collect rows of spectra from the imaging window 110 at regular rotational intervals via a frame grabber 152 (e.g., an LVDS frame grabber). Depending on the speed of the components, the motor 106 can be slowed to allow more time for capture and storage of the rows of spectra. The signal for recording a frame (i.e., a row of spectra) may be supplied directly from the encoder 142 (as indicated by signal path 154), or indirectly through the control computer 118 (as indicated by signal path 156). Imaging is timed to occur when the ingredients within the mixing chamber 102 have fallen against the imaging window 110, at which time they generally do not change position until the mixing chamber 102 has rotated to such an extent that the ingredients begin flowing to the other side of the mixing chamber 102. Depending on the size of the imaging window 110, the size of the field of view desired for imaging, and the lens 140 chosen for the camera 114, each imaged area/pixel typically ranges from 1 cm to 10 cm in diameter (though smaller or larger sizes are possible).

Figure 1C:
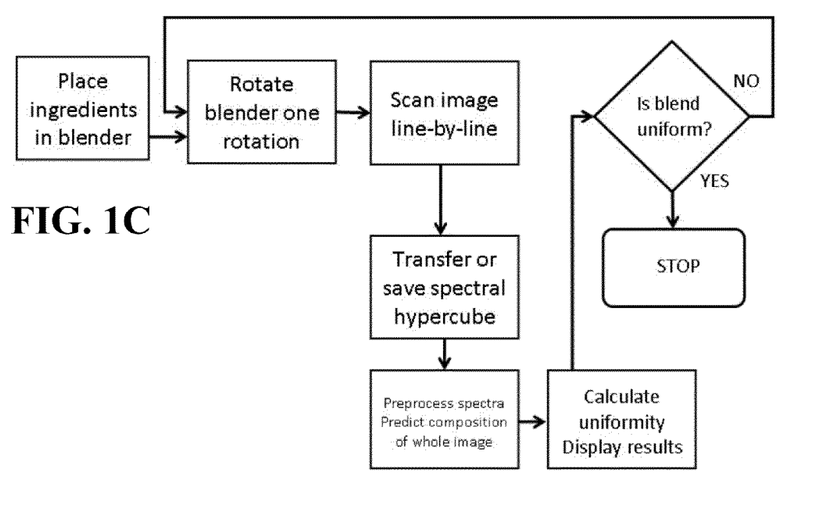
FIG. 1C is a flowchart of an exemplary process for spectrally imaging the blend ingredients being mixed within the mixing chamber 102 and determining the status of the resulting blend.

FIG. 1C depicts a preferred blend monitoring process in greater detail. With each rotation of the mixing chamber 102, a spectral "hypercube" is collected, i.e., a set of spectra wherein each spectrum is captured at a spatial area (pixel) wherein the collection of areas/pixels defines the imaged area across the imaging window 110. The hypercube is transferred to the computer 118 or to another appropriate storage and processing device, where it is either saved or immediately processed (e.g., calibrated versus reference measurements) according to known methods. Different spectra at different areas/pixels indicate different ingredient composition (and thus nonuniformity of the blend), and the spectra can be processed in a number of different ways, described below, to provide indications of blend composition and uniformity. If the results calculated from the hypercube indicate, according to predetermined criteria, that the blending is complete, the blending process can be automatically or manually stopped.

To illustrate in greater detail, a blending system as per FIGS. 1A-1C was constructed using a drum-like one quart mixing chamber 102, situated on a shaft 104 attached to a 10:1 gearbox, which was in turn connected to a stepper motor 106 (M-Drive, Schneider Electric Motion USA). The mixing chamber 102 had a port 108 configured as in FIGS. 1A-1C at its bottom. The imaging window 110 was formed of sapphire having an antireflection coating in the 1000-2500 nm range, and it had a cylindrical curvature close to that of the 18" diameter of the rotating mixing chamber 102, with the window 110 mounted such that the inner and outer window surfaces maintained the same distance in relation to the camera 114 during rotation.

A SWIR hyperspectral camera 114 (Model SWIR-N25-100-LVDS, Specim Ltd, Oulu, Finland) was used with a 31 mm multi-element lens 140 with flat field and color correction in the 1000-2500 nm range (Specim Ltd), though other lenses were found suitable, e.g., a 1:1 imaging lens with flat field correction and color correction in the 1000-2500 nm range (Specim Ltd), or a 2:1 imaging lens with field correction and color correction in the 1000-2500 nm range (Middleton Research, Middleton, Wis.). A flat directing minor 120 with a gold front surface was situated to direct the field of view of the camera 114 to the imaging window 110 on the mixing chamber 102. The camera 114 was focused on the inside of the imaging window 110 to achieve a sharp focus on the ingredients being blended. Two 20 W quartz halogen light sources 112 were mounted in a symmetrical arrangement pointing to viewing windows 122 provided on the housing 124, and in turn to the imaging window 110, and were situated such that the illumination on the imaging window 110 was as uniform and bright as possible. The housing 124, which was formed of stainless steel, enclosed the camera 114, lens 140, minor 120, and light sources 112, as well as the computer 118, camera controller 150, and motor controller 148, and included the aforementioned lateral adjustment mechanism 132 and height adjustment mechanism 134 to allow use of differently sized mixing chambers 102, and to allow for some degree of focus adjustment for the camera.

Datum measurements were then taken for calibration purposes. A port 108 having a reflective (white) reference window was installed on the mixing chamber 102 and its image was recorded, and an image was also captured with the camera shutter closed to provide a dark reference. Each of the pure ingredients for the intended blend—ketoprofen, lactose, methyl cellulose, magnesium stearate and talc—was then imaged in sequence in the mixing chamber 102, with the mixing chamber 102 being cleaned between measurements. In another experiment, the planned blend was prepared and measurements were taken and stored during blending, and datum measurements were subsequently taken for post-blending calibration. Here samples of the blend were mixed together with each of the individual blend ingredients in approximately 90% to 10% proportion, enriching the blend samples with one of the ingredients at a time. After thorough mixing of each blend sample and pure ingredient, each enriched sample was placed in a small sample chamber having an imaging window, and each sample chamber was attached to the mixing chamber to measure the spectral images of the enriched samples. The subtraction of the blend spectra from the enriched blend spectra were then used as calibration spectra for the blend ingredients.

The blend was prepared by weighing its ingredients and placing them in the mixing chamber 102 in the following proportions (by weight):
  10% ketoprofen as active pharmaceutical ingredient (API)
  10% talc as excipients
  10% magnesium stearate
  35% lactose
  35% methyl cellulose The ingredients were then blended in the mixing chamber 102. As the mixing chamber 102 rotated, the encoder 142 provided pulses indicating the position of the mixing chamber 102, and this signal was used to trigger the camera 114 to capture a row of spectra from the imaged material to the entrance slit of the camera 114. A 320×320 pixel hyperspectral image was collected row-by-row, each row containing a full near-infrared spectrum for each of 320 adjacent areas/pixels in the row, and was assembled into a hypercube of data describing the image. 100 such hypercubes were collected, one per rotation for 100 rotations of the mixing chamber 102. At the end of the $100^{th}$ rotation, the mixing chamber 102 was stopped, the camera 114 was retracted from under the mixing chamber 102, and the content of the mixing chamber 102 was emptied.

Figure 2A:
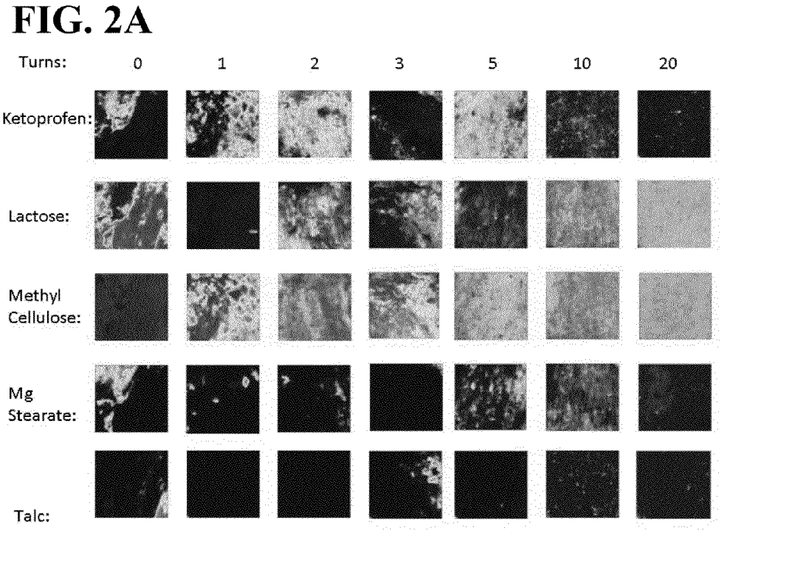
FIG. 2A depicts images of an exemplary blend of ketoprofen, lactose, methyl cellulose, magnesium stearate and talc at 0, 1, 2, 3, 5, 10 and 20 rotations of the mixing chamber of a blending system resembling that of FIGS. 1A-1B, with each image depicting the concentration of each ingredient (with darker areas representing lower concentration and lighter areas representing higher concentration).

Images of each of the rotations of the mixing chamber 102 were constructed from the hypercubes and the calibration data using Matlab™ software and science-based calibration (SBC), a known method for determining the composition of a mixture based on reference spectra taken from blends having known ingredient concentrations, and/or reference spectra taken from pure ingredients (see U.S. Pat. No. 6,629,041). Other spectral chemometric techniques, such as partial least squares (PLS) or classical least squares (CLS), could also or alternatively be used. Separate prediction images (i.e., images illustrating ingredient concentrations calculated from the spectra) were thus produced for each of the ingredients, both API and excipients, for each rotation of the mixing chamber 102. The images were displayed and examined to see the effect of the blending. FIG. 2A shows the images produced for turns 0, 1, 2, 3, 5, 10, and 20, with darker regions showing lower concentration of an ingredient over the imaging window 110, and lighter regions showing higher concentration. (Typically, these images would be presented in color, with different colors representing different concentrations.) It can be seen that for the first three rotations of the mixing chamber 102, the composition is changing drastically because large portions of the pure ingredients cover part of the imaging window 110. By twenty rotations of the mixing chamber 102, the images show much better blending of the particles. Some of the ingredients, such as the ketoprofen for example, still form small aggregates. It can also be seen that the ingredients do not blend at the same rate; methyl cellulose, for example, is non-uniform even after ten turns of the mixing chamber 102. Review of subsequent images up to 100 turns for ketoprofen (these images not being presented here) showed that although ketoprofen distribution became more uniform, small ketoprofen aggregates (seen as light specks) remained.

Figure 2B:
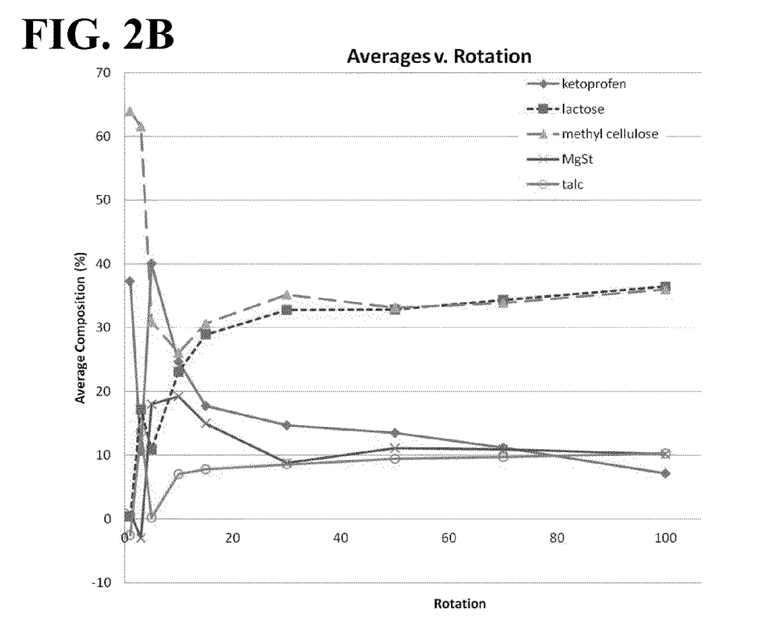
FIG. 2B is a plot of the average blend composition for the exemplary blend of FIG. 2A, as measured/calculated for certain of the 100 rotations of the mixing chamber of a blending system resembling that of FIGS. 1A-1B.

It is noted that review and comparison of the images for all (or even most) rotations is not practical in most industrial applications, and it is therefore beneficial to develop metrics that summarize the progress of blending during the rotations for easier review by blending technicians. Two such metrics are the average blend composition in the prediction image (i.e., the average of the concentration of each ingredient, as derived from the spectra, across the areas/pixels that form the imaged area), and the standard deviation of the individual ingredients (i.e., the standard deviation of each ingredient's concentration, as derived from the spectra, across the areas/pixels that form the imaged area). FIG. 2B presents a plot of the average composition of the aforementioned blend over the 100 rotations, and shows that each ingredient's calculated concentration settles to the nominal values after some initial large deviations prior to about 30 turns. This type of metric, while useful, is not exceptional, as similar metrics can be generated by simply capturing a "bulk" spectrum as in previous blend monitoring systems, i.e., imaging a large field of view across the imaging window 110 such that the captured spectrum represents the average ingredient concentrations across the field of view. Additionally, average blend composition does not indicate whether the ingredients are well blended (i.e., the distribution and uniformity of the blend ingredients), and does not reveal significant information about ingredient blending mechanics. Nonetheless, if a blending technician is merely interested in achieving the nominal blend composition to within a few percent, the calculated average blend composition shows that 30 turns of the mixing chamber may be sufficient.

Figure 2C:
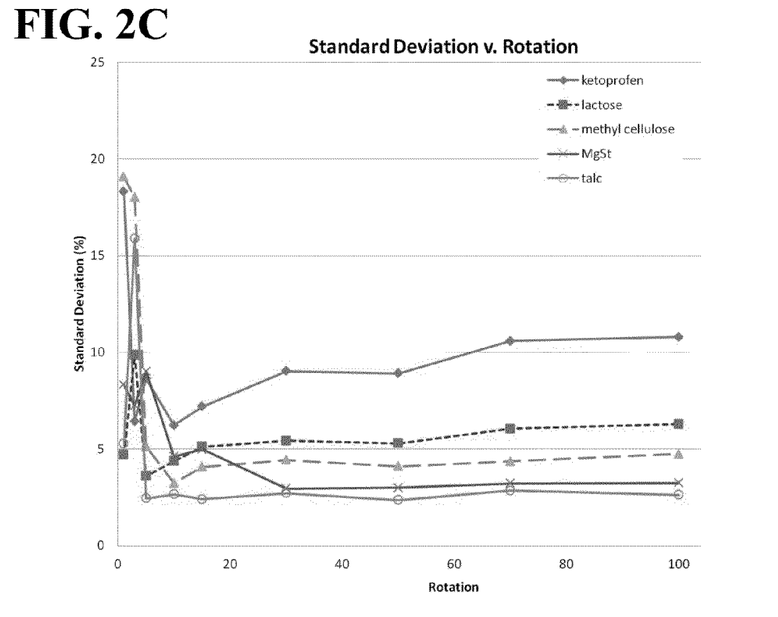
FIG. 2C is a plot of the standard deviation of each of the blend ingredients of FIGS. 2A-2B across the field of view of the camera, and over each of 100 rotations of the mixing chamber of a blending system resembling that of FIGS. 1A-1B.

Standard deviation, as illustrated in FIG. 2C, reveals more information about blending uniformity and mechanics. Here it is seen that while the excipients are fairly well blended by turns 10-15, further blending causes the standard deviation of the ketoprofen to rise, indicating that aggregates are forming as the blending progresses. It may therefore be useful to halt blending after 30 turns or so, when the standard deviation of all other ingredients has settled to about 5% or less (indicating that most of the imaged area is within 5% or so of nominal ingredient concentration). Relative standard deviation, i.e., the standard deviation for each ingredient's concentration divided by its mean (average), is a similar metric which can be used in a similar manner, but relative standard deviation is not illustrated in the accompanying drawings.

Figure 2D:
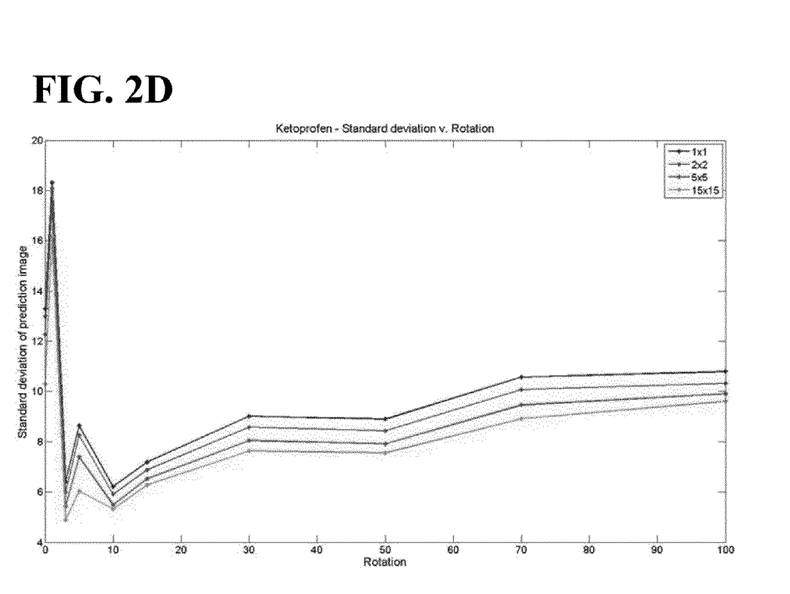
FIG. 2D is a plot of the standard deviation of the ketoprofen within the blend of FIGS. 2A-2C between differently-sized regions across the field of view of the camera.

Another metric that is useful for indicating the distribution of the ingredients within the mixing chamber 102 is shown in FIG. 2D, which illustrates the standard deviation of ingredient concentration (here for ketoprofen) over 100 rotations of the mixing chamber for differently-sized sub-areas of the imaged 320×320 pixel area (a single-pixel area, a 2×2 pixel area, a 5×5 pixel area, etc.). The standard deviations for the areas—which increase as the areas grow smaller—rise as the number of rotations increase (again indicating aggregation), and is higher as the areas grow smaller, showing more variation in (and more aggregation among) smaller areas.

Figure 2E:
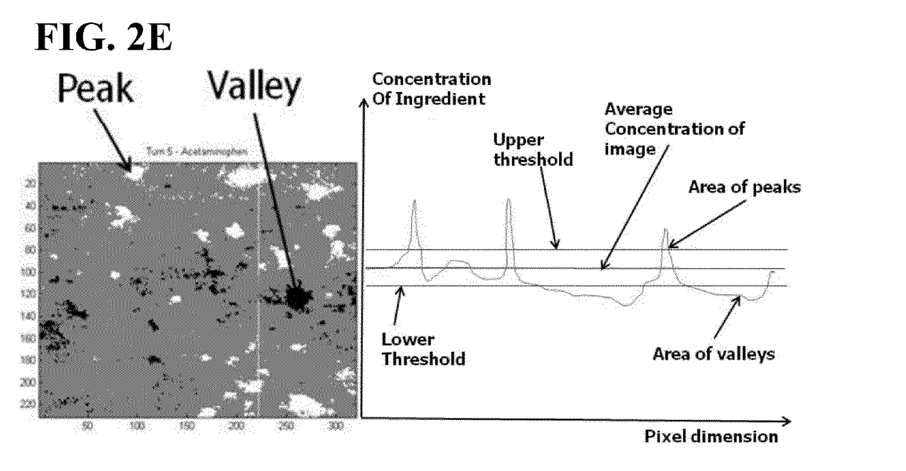
FIG. 2E illustrates an exemplary image of acetominophen concentration (in a blend different from that of FIGS. 2A-2D) across the field of view of the camera, similar to the images of FIG. 2A, wherein concentrations are divided into (and depicted in) white areas of high ("peak") concentrations, black areas of low ("valley") concentrations, and gray regions of intermediate concentrations, along with a plot showing concentration versus area size (pixel number).

FIG. 2E illustrates how the shapes and sizes of agglomerates or "clusters" of an ingredient can be used to generate useful metrics. Clusters of the ingredient (here acetaminophen) are binned into groups: those within a given range of the average concentration of acetaminophen, those above the range ("peaks"), and those below the range ("valleys"). The gray regions in the image at the left of FIG. 2E illustrate areas/pixels within the range near average, and these can be regarded as having close-to-nominal acetaminophen composition. The white regions in the image at the left of FIG. 2E are above a selected higher concentration threshold, and these areas/pixels can be considered acetaminophen aggregates. The black regions in the image at the left of FIG. 2E are below a selected lower concentration threshold, and these areas/pixels can be considered to have low acetaminophen concentration. Analyses of this nature can be used to devise additional useful metrics, including the following:

(1) A percentage of the areas/pixels for each ingredient that are within a certain range of the nominal ingredient concentration (or within a certain range of the mean ingredient concentration over the image, or within a certain range of an arbitrary ingredient concentration). If desired, a blending technician can set a criterion for halting blending if some percentage of the areas/pixels are within some percentage of the desired composition.

(2) A percentage of the areas/pixels for each ingredient that are above a certain threshold relative to the nominal ingredient concentration, the mean ingredient concentration, or an arbitrary ingredient concentration. Since the number of areas/pixels over the threshold can be indicative of the amount of aggregates, this too can be used as a criterion for acceptance of a blend (e.g., a blend could be regarded as completed if all ingredients are below their thresholds).

Figure 2F:
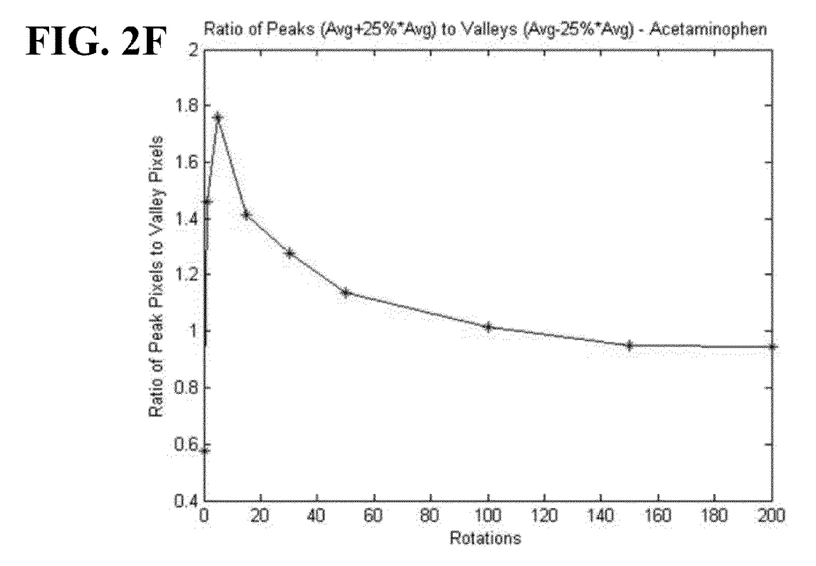
FIG. 2F shows a plot of the ratio of peaks to valleys for the blend of FIG. 2E over time.

(3) The ratio of areas/pixels having high concentrations of an ingredient versus low concentrations of the ingredient (with high concentrations being defined as concentrations above some upper threshold, and low concentrations being defined as concentrations below some lower threshold). This metric provides an indication of the distribution of an ingredient: the ratio increases over a value of 1 as aggregate sizes increase. In an "ideal" blend, one wherein ingredients have more uniform dispersion over time, the ratio for each ingredient should converge on unity as blending proceeds. Referring to FIG. 2F, the ratio of the white (peak or high concentration) areas and black (valley or low composition) areas of FIG. 2E is shown over time for the acetaminophen blend. Here the ratio is changing up to about 150 turns, and then settles to a value very close to one after that, indicating a relatively uniform blend.

(4) Mean, median, and/or maximum of aggregate sizes. Here an aggregate can be defined as a number of adjacent (or closely spaced) areas/pixels having concentration values for an ingredient that exceed that ingredient's nominal or mean concentration (or some arbitrary concentration), perhaps by some threshold. In other words, an aggregate is a cluster of areas/pixels having high concentration of an ingredient. The aggregate size is then defined by the number of areas/pixels exhibiting the excessive concentration, or as this number plus some number of bordering areas/pixels containing some threshold level of the ingredient. This metric is useful since some blends may be unacceptable if they exhibit excessive aggregate sizes. It should be noted that two or more aggregates adjacent each other may register as a single aggregate of large size, and this should be taken into account when considering aggregate size (i.e., when analyzing a distribution of aggregate sizes, high-end outliers might be disregarded since they actually represent multiple aggregates).

(5) Skew and kurtosis of aggregate sizes. Kurtosis is a statistical metric of the "peakedness" of a distribution, and skew is a statistical metric of asymmetry of the distribution. Calculating the kurtosis and skew of aggregate sizes (which can be calculated as discussed above) can inform whether aggregates are prone to form in particular sizes or size ranges, and/or whether they are prone to larger or smaller sizes.

The foregoing (and other) metrics are usefully presented in a graphical form, as in FIGS. 2A-2F, but they can alternatively or additionally be presented in numerical form, e.g., as tables of numerical data.

The foregoing metrics are useful not only for indicating blend completion and blend quality (e.g., blend uniformity), but also reveal useful information about blending mechanics, and possible improvements for blend preparation processes. As an example, if certain ingredients have metrics indicating better dispersion over time (e.g., decreasing standard deviation over time), while others indicate increasing aggregation over time (e.g., increasing standard deviation), this may suggest that the dispersing materials should be blended first, and the aggregating materials added later, with blending then proceeding for the number of turns at which the threshold for unacceptable aggregation previously arose (and with the total number of turns being set to at least the number needed to attain the desired degree of uniformity for the dispersing ingredients). This methodology might allow high uniformity for the dispersing ingredients while preventing formation of unacceptable aggregates, while at the same time minimizing blending time.

The invention can be implemented in any suitable blending systems, including industrial blend production systems, bench-top experimental blending systems, etc. It is known that batch-type blenders can be rescaled to different sizes, but can often still achieve similar blending results, if they have similar Froude numbers Fr (where the Froude number is a measure of inertial stress versus the gravitational force per unit area acting on the material being blended):

$$Fr = N^2 D/g$$

Where
  N=rotation speed [rev's]
  D=diameter of rotating blender vessel [m]
  g=acceleration due to gravity [m/s2]

Thus, a blending scheme can be optimized using a laboratory or pilot scale blender, and can then be scaled up to production scale. When converted to production scale, the invention can be used to monitor and further refine and optimize blending.

Figure 3B:
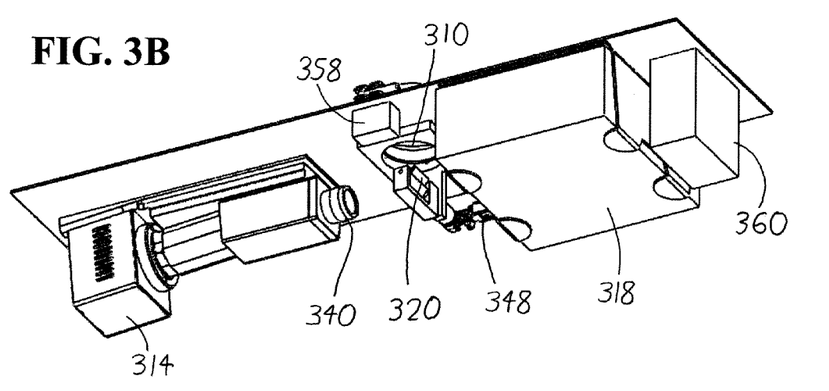
FIG. 3B is a perspective view illustrating the exemplary imaging system of FIG. 3A in greater detail.

FIGS. 3A and 3B then illustrate an alternative version of the blending system of FIGS. 1A-1C wherein the imaging system is mounted directly on the mixing chamber 302, and rotates with it during blending. The housing 324 of the imaging system bears the port 308 of the mixing chamber 302, including its imaging window 310, which separates the blend ingredients from the imaging system. The imaging system includes a push-broom hyperspectral camera 314 (e.g., a near-infrared camera 314 covering the 1000-2000 nm wavelength range) equipped with an imaging spectrograph (not shown) and a short focal length lens 340. The camera 314 is activated to image a row of areas/pixels during the part of the rotation where the imaging window 310 is covered with the blend ingredients, with a pivoting directing minor 320 scanning the row across the imaging window 310. An azimuth detector 358, e.g., an accelerometer or other orientation sensor, can detect these periods during rotation and supply appropriate signals to a motor controller 348 via an onboard processor 318. During the part of the rotation where the imaging window 310 is uncovered or not fully covered, the collected data may be processed by the processor 318, and might be transmitted to an external computer or other processor using a wireless communication. Power might be supplied using a rechargeable battery 360, though an external power source might be used to supply power via suitable conductive rotational coupling.

FIG. 4 then illustrates a continuous blending system wherein a stationary mixing chamber 402 has an actuator (screw or mixing paddles) 406 which both blends the ingredients and pushes them from the inlet port 408A to an outlet port 408B. The imaging system is mounted on the mixing chamber 402 to image its contents through an imaging window 410 via mirror 420. Since the blend will typically be moving at an at least substantially constant speed, the stationary push-broom camera 414 may simply periodically capture an image of a row of areas (via the directing mirror 420), with the row being oriented perpendicular to the blend's direction of travel, to construct an image of the blend as it passes by.

Various preferred versions of the invention are shown and described above to illustrate different possible features of the invention and the varying ways in which these features may be combined. It should be understood that the features of the exemplary blending system of FIGS. 1A-1C, and of the other blending systems, can be modified in numerous ways as appropriate, including variations in the type/shape and size of the mixing chamber 102 and its mounting and sealing arrangement; the type of actuator (motor) 106; the type of agitation applied (e.g., pure rotational orbits versus trochoids, cycloids, or other orbits, combinations of rotation and translation, etc.); the type of camera 114 and the components used to image the imaging window 110; etc. Following are several additional exemplary modifications.

The directing mirror 120 of FIG. 1A need not be stationary, and can be a moving minor which directs the field of view of the camera 114 as desired. For example, the rotation of the mixing chamber 102 might be stopped while the image of the imaging window 110 is scanned, with the directing mirror 120 pivoting to scan the camera's linear field of view across the imaging window 110.

Rather than having a linear field of view in which a row of areas/pixels is imaged, the camera 114 of FIG. 1A may be of the "staring array" type, wherein a two-dimensional array of areas/pixels is imaged using sequential wavelength tuning. In other words, rather than scanning across an area while simultaneously measuring the intensities of light across all wavelengths of interest, the area is imaged while scanning across wavelengths of interest. Typically, light intensity from the blend is measured one wavelength at a time with a tunable filter placed in the light collection path between the camera 114 and the blend (e.g., an acousto-optic tunable filter, a liquid crystal tunable filter, a Fabry-Perot tunable filter, or any other wavelength selection device, such as a continuously variable thin-film band-transmission filter). Alternatively, the blend can be illuminated one wavelength at a time, as with a wavelength tunable laser, and the reflected/transmitted/non-absorbed light from the blend is then measured. Here the mixing chamber 102 must typically be halted during collection of measurements because the wavelength tuning can be time-consuming, and motion of the imaging window 110 (and the ingredients therein) during the collection of an image may lead to inaccuracies (e.g., a mixture may tumble off of the imaging window 110 before a complete hypercube can be assembled). Use of a staring array is also disadvantageous in that it typically requires that the light source 112 illuminate the area being imaged for the duration of the measurement, which can result in undesirable energy input (e.g., heating) to the blend. In contrast, "push-broom"-style imaging only needs to briefly illuminate the imaged area a row at a time.

Regardless of whether area scanning or wavelength scanning is used, the camera 114 is not limited to capturing spectra in the near-infrared (NIR) range, i.e., the 1000-1700 nm range, or the short-wave infrared (SWIR) range, i.e., the 1000-2500 nm range, and other wavelength ranges such as 400-1000 nm (VNIR) or 200-400 nm (UV) may be imaged as needed (with choice of suitable components). Raman spectroscopy might alternatively or additionally be used, in which case a light source 112 in the form of a strong monochromatic laser might be scanned row by row across an area of interest within the imaging window 110 (with the laser preferably having a line filter to limit illumination of the blend ingredients to the laser light). Raman scatter from the blend ingredients can then be collected with a collection mirror 120, and directed through a notch rejection filter onto a sensitive camera 114 suitable for Raman spectral measurements. A Raman spectral hypercube can then be assembled one spatial row at a time. Since a Raman system can have better focus due to the shallower light penetration depth and the shorter wavelengths used to generate the Raman radiation, smaller area/pixel sizes may be used, allowing better discrimination of individual ingredient particles within the blend. Since the Raman effect is related to the fundamental vibrations of the molecules being illuminated, it may also yield more chemical differentiation than where near-infrared reflectance spectroscopy is used. As another option, fluorescence spectroscopy might be used, with an ultraviolet source illuminating the blend through the imaging window 110. Fluorescence induced by the ultraviolet light can be detected row by row using a suitable camera 114. Here too smaller area/pixel sizes may be possible since cameras 114 for measuring fluorescence in the visible range tend to have higher spatial resolution than near-infrared cameras 114, and their lenses and other optics can often yield higher resolution due to the shorter wavelengths involved.

The invention is not intended to be limited to the preferred versions described above, but rather is intended to be limited only by the claims set out below. Thus, the invention encompasses all different versions that fall literally or equivalently within the scope of these claims.

What is claimed is:

1. A blending system including:
    a. a blender configured to mix ingredients therein, the blender having:
        (1) a mixing chamber configured to receive ingredients for mixing, wherein the mixing chamber defines a mixing bin wherein ingredients to be mixed may be fully enclosed, and
        (2) a solid imaging window situated on the mixing chamber, the imaging window being at least substantially transparent to one or more wavelengths of light;
    b. a light source aligned with the imaging window to illuminate any ingredients within the mixing chamber;
    c. a camera aligned with the imaging window, the camera being configured to capture a set of spectra from any ingredients within the mixing chamber, each spectrum within the set being captured from a different area next to the imaging window, wherein the camera is spaced from the mixing chamber;
    d. a processor configured to:
        (1) receive the spectra, and
        (2) generate a display from the spectra, the display being indicative of the distribution of the ingredients within the mixing chamber;
    e. an actuator configured to:
        (1) move the mixing chamber to agitate any ingredients therein, and
        (2) move the mixing chamber along a path which periodically aligns the camera with the imaging window, wherein the camera is stationary during motion of the mixing chamber.

2. The blending system of claim 1 wherein the processor is configured to generate a display from the spectra, the display including an image representing changes over time in spectral intensity at two or more wavelengths.

3. The blending system of claim 1 wherein the processor is configured to generate a display from the spectra, the display including sets of images wherein:
    a. each set contains images representing spectra obtained during at least substantially the same time,
    b. different sets contain images representing spectra obtained at different times,
    c. each image within each set represents:
        (1) a field within the mixing chamber next to the imaging window, the field corresponding to the different areas, and
        (2) the spectral intensity at each area at the same wavelength,
    d. the different images within each set depict the spectral intensity at each area over the field at a different wavelength.

4. The blending system of claim 1 wherein the camera is configured to capture rows of spectra with:
    a. the rows being successively captured in sequence, and
    b. each row containing spectra from adjacent areas next to the imaging window.

5. The blending system of claim 4:
a. further including a port openable and closable onto the mixing chamber,
b. wherein the imaging window is situated on the port.

6. The blending system of claim 4:
a. wherein the mixing chamber has an inlet port and an exit port;
b. further including an actuator configured to move ingredients to be mixed through the mixing chamber from the inlet port through the exit port.

7. The blending system of claim 4 wherein the camera is mounted in a fixed position relative to the imaging window.

8. The blending system of claim 7:
a. wherein the mixing chamber defines a mixing bin wherein ingredients to be mixed may be fully enclosed, and whereupon the camera is mounted;
b. further including an actuator configured to move the mixing chamber to agitate any ingredients therein.

9. The blending system of claim 1 wherein the camera is configured to capture rows of spectra with:
a. the rows being successively captured in sequence, and
b. each row containing spectra from adjacent areas next to the imaging window.

10. The blending system of claim 1 wherein:
a. the camera is mounted to move with the mixing chamber, and
b. the actuator is configured to decrease the speed at which the mixing chamber moves when the imaging window is situated at least partially vertically above the camera.

11. The blending system of claim 1 wherein the actuator is configured to rotate the mixing chamber about a tumbling axis.

12. The blending system of claim 11 wherein the camera is configured to capture rows of spectra with:
a. the rows being successively captured in sequence, and
b. each row containing spectra from adjacent areas next to the imaging window, wherein each captured spectrum is from one of the areas.

13. The blending system of claim 11 wherein:
a. the imaging window has an interior surface adjacent a mixing chamber interior and an exterior surface outside the mixing chamber, and
b. the interior surface is curved, whereby an at least substantially constant distance is maintained between the interior surface and the camera during rotation of the mixing chamber.

14. The blending system of claim 11:
a. further including a reference window on the mixing chamber, the reference window being:
(1) spaced from the imaging window, and
(2) situated to periodically align with the camera;
b. wherein:
(1) the camera is further configured to capture a reference spectrum from the reference window;
(2) the processor is configured to adjust the received spectra in dependence on the reference spectrum.

15. The blending system of claim 14 wherein the reference window has a curved exterior surface, whereby an at least substantially constant distance is maintained between the exterior surface of the reference window and the camera during rotation of the mixing chamber.

16. A blending system including:
a. a blender configured to mix ingredients therein, the blender having:
(1) a mixing chamber configured to receive ingredients for mixing, wherein the mixing chamber defines a mixing bin wherein ingredients to be mixed may be fully enclosed, and
(2) a solid imaging window situated on the mixing chamber, the imaging window being at least substantially transparent to one or more wavelengths of light;
b. a light source aligned with the imaging window to illuminate any ingredients within the mixing chamber;
c. a camera aligned with the imaging window, the camera being configured to capture a set of spectra from any ingredients within the mixing chamber, each spectrum within the set being captured from a different area next to the imaging window, wherein the camera is spaced from the mixing chamber;
d. a processor configured to:
(1) receive the spectra, and
(2) generate a display from the spectra, the display being indicative of the distribution of the ingredients within the mixing chamber;
e. an actuator configured to:
(1) move the mixing chamber to agitate any ingredients therein,
(2) move the mixing chamber along a path which periodically aligns the camera with the imaging window, wherein the camera is stationary during motion of the mixing chamber, and
(3) move the mixing chamber at a slower speed when the camera is aligned with the imaging window.

17. A blending system including:
a. a blender having:
(1) a mixing chamber defining an enclosure for receiving ingredients to be mixed, the mixing chamber including:
(a) a port openable onto and closable upon the mixing chamber,
(b) an imaging window situated on the mixing chamber, the imaging window allowing transmission of one or more wavelengths of light into and out of the mixing chamber;
(2) an actuator configured to move the mixing chamber to agitate any ingredients therein;
b. a light source situated adjacent the mixing chamber, whereby the light source periodically illuminates the imaging window during motion of the mixing chamber;
c. a stationary camera:
(1) mounted adjacent the mixing chamber,
(2) being configured to periodically capture a set of spectra from any ingredients within the mixing chamber next to the imaging window, the spectra being captured from contiguous areas next to the imaging window, wherein each captured spectrum is from one of the areas;
d. a processor configured to generate from the spectra a measure of the uniformity of the distribution of the ingredients within the mixing chamber.

18. A blending system including:
a. a blender with:
(1) a mixing chamber defining an enclosure for receiving ingredients to be mixed,
(2) an actuator configured to rotate the mixing chamber about a tumbling axis,
(3) an imaging window on the mixing chamber through which one or more wavelengths of light may be transmitted into and out of the mixing chamber, the imaging window having a curved inner window surface;

b. a stationary camera:
   (1) situated adjacent a path traveled by the imaging window during rotation of the mixing chamber,
   (2) being aligned to periodically image the imaging window to capture successive sets of spectra from any ingredients within the mixing chamber next to the imaging window, each set containing spectra from a row of areas next to the imaging window, and
   (3) having a fixed focus on or adjacent to the curved inner window surface during rotation of the mixing chamber;
c. a processor configured to assemble the sets of spectra into sets of images wherein:
   (1) each set contains images representing spectra obtained after the same number of rotations of the mixing chamber,
   (2) different sets contain images representing spectra after different numbers of rotations of the mixing chamber,
   (3) each image within each set represents:
      (a) a field within the mixing chamber next to the imaging window, the field corresponding to the rows of areas, and
      (b) the spectral intensity at each area at the same wavelength,
   (4) the different images within each set depict the spectral intensity at each area over the field at a different wavelength.

* * * * *